United States Patent [19]

Kovacevic et al.

[11] Patent Number: 5,446,038
[45] Date of Patent: Aug. 29, 1995

[54] 5-THIA-1,4-DIAZABICYCLO[4.2.0]OCTANE-3,8-DIOXO ANALOGS OF β-LACTAM, PROCESSES FOR THE PREPARATION THEREOF AND THE USE THEREOF

[75] Inventors: Miće Kovačević; Jure J. Herak; Zora Mandić; Irena Lukić; Mirjana Tomić; Zinka Brkić, all of Zagreb, Croatia

[73] Assignee: PLIVA, farmaceutska, kemijska, prehrambena i kozmeticka industrija dionicko, Croatia

[21] Appl. No.: 151,673

[22] Filed: Nov. 12, 1993

[30] Foreign Application Priority Data

Nov. 17, 1992 [HR] Croatia .................. P921292A

[51] Int. Cl.⁶ .................................. C07D 513/04
[52] U.S. Cl. ............................. 514/210; 540/214
[58] Field of Search .............. 540/214, 215, 310; 514/210

[56] References Cited

U.S. PATENT DOCUMENTS

4,576,939  3/1986  Ross et al. ..................... 540/214

FOREIGN PATENT DOCUMENTS

WO94/05632  3/1994  WIPO .

OTHER PUBLICATIONS

Campbell, et al., 2–Azacephems, Tetrahedron, vol. 46, No. 11, (1990), pp. 3973–3980.
Ross, et al., Penem derivatives, Eur. Pat. Appl. EP 31,509, 28–Heterocycles, vol. 96, 1982, p. 669.
Sempuku, Cephalosporin–related compounds, Dainippon Pharmaceutical Co., Ltd., Jpn. Kokai Tokkyo Koho JP 59 01,491, Chemical Abstracts, vol. 101 (1984) p. 624.
Gregory, Recent Advances in the Chemistry of β-Lactam Antibiotics, Special Publication No. 38, Cambridge, England, 30th Jun.–2nd Jul., 1980.
Campbell, et al., New Reaction of Penicillins: the Formation, and Crystal and Molecular Structure of a β-Lactam-fused Heterocyclic Ylide, J. C. S. Chem. Comm., 1974, p. 868.
Campbell, et al., Transformations of Penecillins: Reactions with Chloramine T, J. C. S. Perkin I, p. 1208.
Doyle, et al., Nuclear analogs of β-lactam antibiotics. VI. Synthesis of N-2-isocephems. Can. J. Chem. vol. 55 (1977).

*Primary Examiner*—Nicholas Rizzo
*Attorney, Agent, or Firm*—Pollock, Vande Sande & Priddy

[57] ABSTRACT

5-Thia-1,4-diazabicyclo[4.2.0]octane-3,8-dioxo analogs of β-lactam, processes for the preparation thereof and the use thereof Disclosed are novel 5-thia-1,4-diazabicyclo[4.2.0]octane-3,8-dioxo β-lactam analogs of the general formula I

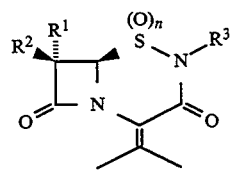

wherein
$R^1$ is hydrogen or halo;
$R^2$ is hydrogen, halo, amino, $PhCH_2CONH$, $PhOCH_2CONH$, phthalimido, $o\text{-}MeNHCO\text{-}C_6H_4\text{-}CONH$, isoxazolylcarboxamido;
$R^3$ is hydrogen, alkyl, benzyl, heterocycle, e.g. isoxazole, pyrazole etc., and
n may be 1 or 2.

They may be used as intermediates in preparing novel β-lactam analogs or as active substances in formulations for antimicrobial therapy.

14 Claims, No Drawings

5-THIA-1,4-DIAZABICYCLO[4.2.0]OCTANE-3,8-DIOXO ANALOGS OF β-LACTAM, PROCESSES FOR THE PREPARATION THEREOF AND THE USE THEREOF

TECHNICAL FIELD

The present invention relates to 5-thia-1,4-diazabicyclo[4.2.0]octane-3,8-dioxo-3,8-dioxo-5-oxides and -5,5-dioxides, to the processes for the preparation thereof as well as to the use thereof. These compounds are novel β-lactam analogs of bicyclic structure formed by β-lactam ring and thiadiazine ring. As far as we are aware of the prior art, 5-thia-1,4-diazabicyclo[4.2.0]octane-3,8-dioxo analogs of β-lactam and, consequently, also processes for the preparation thereof are not known.

The most similar known compounds are 5-thia-1,4-diazabicyclo[4.2.0]octane-8-oxo analogs of β-lactam, i.e. 2-azacephems [Tetrahedron 46 (1990) 3973–3980; EP 31509 (1979); JP 5901491 (1984)]. Said compounds are obtained by chemical transformations of thiazolidine ring of the natural penicillin or known β-lactam intermediates such as 6-aminopenicillanic acid. There are also known 3-azacephems [Spec. Pub. R.C.S. No. 38 (1981) 97–108], which are also obtained from penicillin via thiazolineazetidinone intermediate. There are also obtained 4-thia-1,5-diazabicydlo[4.2.0]-octane-8-oxo analogs of β-lactam, i.e. 1-aza-2-thiacephems [J.C.S. Chem. Commun. (1974) 868; J.Chem. Soc. Perkin Trans 1 (1975) 1208], as well as 1-carba-2-azacephems [Can. J. Chem. 55 (1977) 2719] and various other bicyclic β-lactam analogs.

The object of the present invention are 5-thia-1,4-diazabicyclo[4.2.0]octane-3,8-dioxo β-lactam analogs of the general formula I,

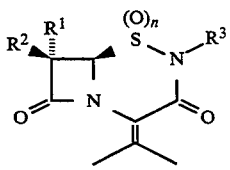

wherein
$R^1$ is hydrogen or halo;
$R^2$ is hydrogen, halo, amino, $PhCH_2CONH$, $PhOCH_2CONH$, phthalimido, o-$MeNHCO$-$C_6H_4$-$CONH$, isoxazolylcarboxamido;
$R^3$ is hydrogen, alkyl, benzyl, heterocycle, e.g. isoxazole, pyrazole etc., and
n may be 1 or 2.

A further object of the present invention is a process for preparing 5-thia-1,4-diazabicyclo[4.2.0]octane-3,8-dioxo analogs of β-lactam of the general formula I, wherein the radicals have the above meaning, which compounds may be prepared by intramolecular cyclization of the functional groups in the $N_1$- and $C_2$-position of aminosulfonyl and aminosulfinyl 4-oxo-azetidines, resp., of the general formula II,

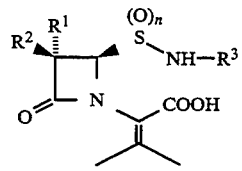

wherein
$R^1$ is hydrogen or halo;
$R^2$ is hydrogen, halo, amino, $PhCH_2CONH$, $PhOCH_2CONH$, phthalimido, o-$MeNHCO$-$C_6H_4$-$CONH$, isoxazolylcarboxamido;
$R^3$ is hydrogen, alkyl, benzyl, heterocycle, e.g. isoxazole, pyrazole etc., and
n may be 1 or 2.

The compounds of the general formula II are subject-matter of our German Patent Application P 42 30 053.3 of Sep. 8, 1992 entitled "4-oxo-azetidine 2-sulfonic acid amides and salts thereof, processes for the preparation thereof and the use thereof". The tendency of said compounds to be cyclized into novel bicyclic β-lactam analogs of the general formula I was found whilst activating the carboxylic function of said compounds. The process of activating the carboxylic function of the compounds of the formula II is carried out by means of conventional methods of forming active esters, acid chlorides, mixed anhydrides and other suitable carboxylic derivatives which, obtained in situ, are cyclized in a dry organic solvent to yield the compounds of the general formula I. The activation of the carboxylic function of some compounds II and the cyclization into corresponding compounds I are also carried out in situ whilst deblocking the carboxylic function, e.g. whilst cleaving the benzylic protective group with aluminum trichloride. All reactions take place under conventional reaction conditions and the products obtained are isolated after treating the reaction mixture by means of crystalization or chromatography on a silica gel column.

Another object of the present invention is the use of the said compounds as useful intermediates in the process for preparing novel potential β-lactam antibiotics or as synergists of β-lactam antibiotics. This relates especially to the possibility of a modification of the functional groups on $C_2$, $C_3$ and $C_7$ atoms of the compounds of the general formula I as well as to other possibilities provided by said substrates.

A further object of the present invention relates to the use of said compounds as potential active materials in ready-for-use pharmaceuticals having antimicrobial action. Some of these products show synergistic activity with ampicillin.

Further investigations of the relation between the structure and the antimicrobial activity of the β-lactam analogs of the general formula I will show the effect of a synergistic action of said compounds with other β-lactam antibiotics as well.

EXAMPLE 1

(6R,7R)
5-Thia-1,4-diazabicyclo[4.2.0]octane-2-isopropylidene-4-benzyl-7-phenylacetamido-3,8-dioxo-5,5-dioxide (2R,3R) 1(1'-Carboxyl-2'-methyl-prop-1'-enyl)-2-benzylaminosulfonyl-3-phenylacetamido-4-oxo-azetidine (350 mg, 0.74 mmole) was dissolved in methylene chloride (10 ml), a solution of dicyclohexylcarbodiimide (185 mg, 0.90 mmole) in methylene chloride (10 ml) was added and it was stirred for 1 hour at the room temperature. The precipitate obtained was sucked off and the mother liquor was washed with a saturated aqueous sodium bicarbonate solution. The organic part was washed with water, dried ($Na_2SO_4$), filtered and evaporated in vacuo. The residue was chromatographed on a silica gel column under elution with the methylene chloride/ethyl acetate (9:1) solvent mixture. 314 mg (93.2%) of the product were obtained: m.p. 176°–178° C.; $R_f$0.61 ($CH_2Cl_2$:EtOAc=9:1).

IR (KBr): 3290m, 3040w, 2960w, 1795s, 1695m, 1670s, 1620w, 1530m, 1505w, 1460w, 1435w, 1365s,1350m, 1240w, 1170s, 1120w, 1035w, 1005w, 880w, 755w, 700m $cm^{-1}$;

300 MHz $^1$H NMR ($CDCl_3$) δ:2.03 and 2.32 (6H, 2s, $CMe_2$), 3.65 (2H, bs, $CH_2CO$), 4.91 and 4.98 (2H, ABq, J 15.2 Hz, $NCH_2$), 4.98 (1H, d, J 4.3 Hz, $C_6H$), 6.16 (1H, dd, J 4.3 in 10 Hz, $C_7H$), 6.64 (1H, d, J 10 Hz, CONH), 7.26–7.42 (10H, m, 2 $C_6H_5$) ppm;

m/e 453 ($M^+$+1);

Analysis for $C_{23}H_{23}N_3O_5S$ (453.51) calc.: C 60.91; H 5.11; N 9.26; S 7.07% found: C 61.04; H 5.31; N 9.15; S 7.55%

EXAMPLE 2

(6R, 7R)
5-Thia-1,4-diazabicyclo[4.2.0]octane-2-isopropylidene-4(5′-methyl-isoxazole-3′-yl)-7-phenylacetamido-3,8-dioxo-5,5-dioxide (2R,3R) 1 (1′-Carboxyl-2′-methyl-prop-1′-enyl)-2-[(5′-methyl-isoxazole-3′-yl)-aminosulfonyl]-3-phenylacetamido-4-oxo-azetidine (300 mg, 0.65 mmole) was dissolved in methylene chloride (10 ml) and subjected to a reaction with dicyclohexylcarbodiimide, analogously to the above procedure. 170 mg (58.5%) of the product were obtained: m.p. 180°–183° C.; $R_f$0.53 ($CH_2Cl_2$:EtOAc=4:1).

IR (KBr): 3300m, 3030w, 2960w, 2920w, 1790s, 1715s, 1670s, 1610m, 1520m, 1500w, 1450–1430bw, 1420w, 1380s, 1360m, 1265w, 1250m, 1220w, 1200w, 1170s, 1135w, 1100w, 1065w, 1020w, 975w, 925w, 890w, 795w, 770w $cm^{-1}$;

300 MHz $^1$H NMR ($CDCl_3$) δ:2.09 and 2.33 (6H, 2s, $CMe_2$), 2.48 (3H, s, Me-isoxazole), 3.64 (2H, bs, $CH_2CO$), 5.28 (1H, d, J 4.3 Hz, $C_6H$), 6.10 (1H, s, CH-isoxazole), 6.27 (1H, dd, J 4.3 and 10 Hz, $C_7H$), 6.75 (1H, d, J 10 Hz, CONH), 7.22–7.37 (5H, m, $C_6H_5$) ppm.

EXAMPLE 3

(6R, 7R) 5-Thia-1,4-diazabicyclo[4.2.0]octane-2-isopropylidene-4-methyl-7-phenyl acetamido-3,8-dioxo-5,5-dioxide (2R,3R) 1(1′-Carboxyl-2′-methyl-prop-1′-enyl)-2-methylaminosulfonyl]-3-phenylacetamido-4-oxo-azetidine (310 mg, 0.78 mmole) was dissolved in methylene chloride and subjected to the reaction with dicyclohexylcarbodiimide analogously to the procedure of Example 1. 225 mg (59.6%) of a white powder were obtained: $R_f$0.67 ($CH_2Cl_2$:EtOAc=4:1);

IR (KBr): 3310m, 3040w, 2960w, 1785s, 1700s, 1660s, 1620m, 1520s, 1500m, 1445w, 1360m, 1270m, 1240m, 1210w, 1160m, 1120w, 1075w, 1005m, 990w, 930w, 890m, 855w, 825w, 780w, 755w, 735m, 700m, 675m $cm^{-1}$;

300 MHz $^1$H NMR ($CDCl_3$) δ:2.04 and 2.34 (6H, 2s, $CMe_2$), 3.19 (3H, s, NMe), 3.65 (2H, bs, $CH_2CO$), 4.97 (1H, d, J 4.3 Hz, $C_6H$), 6.19 (1H, dd, J 4.3 and 10.4 Hz, $C_7H$), 6.72 (1H, d, J 10.4 Hz, CONH), 7.25–7.39 (5H, m, $C_6H_5$) ppm;

m/e 377 ($M^+$+1).

EXAMPLE 4

(6R,7R)5-Thia-1,4-diazabicyclo[4.2.0]octane-2-isopropylidene-4(5′-methyl-isoxazole-3′-yl)-7-phthalimido-3,8-dioxo-5,5-dioxide (2R,3R) 1(1′-Carboxyl-2′-methyl-prop-1′-enyl)-2-[(5′-methyl-isoxazole-3′-yl)-aminosulfonyl]-3-phthalimido-4-oxo-azetidine (240 mg, 0.5 mmole) was dissolved in tetrahydrofuran (5 ml) and subjected to the reaction with dicyclohexylcarbodiimide analogously to the procedure of Example 1. A foamy product (137 mg; 60%) was obtained, which crystallized from methanol: m.p. 195°–197° C.; $R_f$0.91 ($CH_2Cl_2$:MeOH=9:1);

IR (KBr): 1815s, 1790m, 1740vs, 1725s, 1610m, 1430w, 1390s, 1370s, 1255w, 1215w, 1175s, 1110m, 1010w, 915w, 800w, 760w, 720m, 710m, 655m $cm^{-1}$;

300 MHz $^1$H NMR ($CDCl_3$) δ:2.20 and 2.39 (6H, 2s, $CMe_2$), 2.46 (3H, s, Me-isoxazole), 5.41 (1H, d, J 4.4 Hz, $C_6H$), 6.01 (1H, d, J 4.4 Hz, $C_7H$), 6.27 (1H, s, CH-isoxazole), 7.68–7.92 (4H, m, Pht) ppm.

EXAMPLE 5

(6R,7R)
5-Thia-1,4-diazabicyclo[4.2.0]octane-2-isopropylidene-4-methyl-7-o-methylamino-carbonylphenylcarboxamido-3,8-dioxo-5,5-dioxide (2R,3R) 1(1′-Carboxyl-2′-methyl-prop-1′-enyl)-2-methylaminosulfonyl]-3-o-methyl-aminocarbonylphenylcarboxamido-4-oxo-azetidine (440 mg, 1 mmole) was dissolved in methylene chloride (15 ml) under the addition of triethylamine (110 mg, 1.1 mmole) and cooled to −10° C. Ethyl chloroformate (120 mg, 1.1 mmole) was added to the reaction mixture whilst stirring and then the stirring was continued for 1 hour at the temperature of −10° C. and for 1.5 hours at room temperature. The reaction mixture was evaporated to dryness in vacuo. The residue was chromatographed on a silica gel column, eluting with a methylene chloride/methanol (19:1) solvent mixture. A foamy product (367 mg, 87.4%) was obtained, which crystallized from methanol: m.p. 212°–214° C.; $R_f$0.67 ($CH_2Cl_2$: MeOH=9:1);

IR (KBr): 3310vs, 1795vs, 1690s, 1670s, 1645s, 1540sh, 1520s, 1370s, 1330m, 1250m, 1165s, 1000m, 910m, 785w, 760m, $cm^{-1}$;

300 MHz $^1$H NMR ($CDCl_3$) δ:2.09 and 2.37 (6H, 2s, $CMe_2$), 3.01 (3H, d, J 4.9 Hz, CONMe), 3.24 (3H, s, $SO_2NMe$), 5.13 (1H, d, J 4.3 Hz, $C_6H$), 6.22 (1H, b, CONH), 6.33 (1H, dd, J 4.3 and 9.6 Hz, $C_7H$), 7.48–7.68 (4H, m, $C_6H_4$), 7.77 (1H, d, J 9.6 Hz, CONH) ppm;

m/e 420 ($M^+$).

EXAMPLE 6

(5R,6R)
5-Thia-1,4-diazabicyclo[4.2.0]octane-2-isopropylidene-4-benzyl-3,8-dioxo-5-oxide An epimeric mixture of (2R) 1(1′-carboxyl-2′-methyl-prop-1′-enyl)-2-benzylamino-sulfinyl-4-oxo-azetidine (970 mg, 3 mmole) having $R_f$ values 0.24 and 0.30 (EtOH:MeOH=3:1), obtained from the corresponding benzyl esters by a reaction with aluminum trichloride according to the process described in Example 10 of our German Patent Application P 42 30 053.3 (Sep. 8, 1992), was dissolved in methylene chloride and cooled to −10° C. To the solution triethylamine (333 mg, 3.3 mmole) was added and a solution of ethyl chloroformate (651 mg, 6 mmole) in methylene chloride (5 ml) was added drop by drop and it was stirred for 1 hour at −10° C. The reaction mixture was washed with cold water (20 ml), with 1N hydrochloric acid and again with cold water. The organic extract was dried over sodium sulfate, filtered and evaporated to dryness in vacuo. There were obtained 1068 mg (90%) of the mixture of epimeric mixed anhydrides with $R_f$ values 0.32 and 0.43 ($CH_2Cl_2$:EtOAc=2:1). The epimer having $R_f$ value 0.43 [IR (film): 3210w, 2980w, 1800vs, 1775vs, 1620w, 1360s, 1240m, 1150vs, 1060s, 1020s, 980m cm$^{-1}$;

300 MHz $^1$H NMR (CDCl$_3$) δ:1.37 (3H, t, J 7.1 Hz, Me), 2.16 and 2.28 (6H, 2s, CMe$_2$), 3.08 (1H, dd, J 2.5 and 15.6 Hz, βC$_3$H), 3.26 (1H, dd, J 5.5 and 15.6 Hz, αC$_3$H), 4.15 (1H, 2d, J 5.0 and 6.1 Hz, NH), 4.28 and 4.35 (2H, 2dd, J 5.0, 6.1 and 14.1 Hz, CH$_2$Ph), 4.34 (2H, q, J 7.1 Hz, CH$_2$), 4.87 (1H, 2d, J 2.5 and 5.5 Hz, C$_2$H), 7.28–7.35 (5H, m, C$_6$H$_5$) ppm] (790 mg, 2 mmole) was dissolved in dry methylene chloride (20 ml) and at room temperature triethylamine (222 mg, 2.2 mmole) in methylene chloride (5 ml) was added drop by drop. After stirring at room temperature for 1 hour, the reaction mixture was washed with 1N hydrochloric acid (20 ml) and water, dried over sodium sulfate and evaporated to dryness. There were obtained 500 mg of dark brown product, which was passed through a silica gel column, eluting with a methylene chloride/ethyl acetate mixture. A crystalline product (225 mg; 37%) was obtained: m.p. 164°–166° C.; $R_f$ 0.70 ($CH_2Cl_2$:EtOAc=2:1);

IR (film): 1775vs, 1670s, 1610m, 1390m, 1355s, 1270m, 1230s, 1140m, 1080s, 1020m cm$^{-1}$;

300 MHz $^1$H NMR (CDCl$_3$) δ:2.08 and 2.30 (6H, 2s, CMe$_2$), 3.20 (1H, dd, J 1.0 and 15.3 Hz, βC$_7$H), 3.39 (1H, dd, J 4.3 and 15.3 Hz, αC$_7$H), 4.65 and 5.21 (2H, 2d, J 15.0 Hz, CH$_2$Ph), 4.78 (1H, dd, J 1.0 and 4.3 Hz, C$_6$H), 7.33 (5H, s, C$_6$H$_5$) ppm.

EXAMPLE 7

(5S,6R)5-Thia-1,4-diazabicyclo[4.2.0]octane-2-isopropylidene-4-benzyl-3,8-dioxo-5-oxide The epimer of the mixed anhydride from Example 6 having $R_f$ value of 0.32 [IR (film): 3215w, 2990w, 1800vs, 1780vs, 1620w, 1360s, 1250m, 1150vs, 1060s, 1025s, 985m cm$^{-1}$; 300 MHz $^1$H NMR (CDCl$_3$) δ:1.36 (3H, t, J 7.1 Hz, Me), 2.00 and 2.27 (6H, 2s, CMe$_2$), 3.24 (1H, dd, J 5.2 and 15.4 Hz, αC$_3$H), 3.43 (1H, dd, J 2.2 and 2d, J 5.7 and 6.0 Hz, NH), 4.34 (2H, q, J 7.1 Hz, CH$_2$), 4.87 (1H, 2d, J 2.2 and 5.2 Hz, C$_2$H), 7.26–7.35 (5H, m, C$_6$H$_5$) ppm] was subjected to the reaction and treated as disclosed in Example 6. There was obtained an oily product $R_f$ 0.65 (CH$_2$Cl$_2$: EtOAc=2:1);

IR (film): 1780vs, 1675m, 1610m, 1380m, 1355s, 1275m, 1230s, 1140m, 1080s, 1020m cm$^{-1}$;

300 MHz $^1$H NMR (CDCl$_3$) δ:2.06 and 2.33 (6H, 2s, CMe$_2$), 2.92 (1H, dd, J 2.5 and 16.5 Hz, βC$_7$H), 3.50 (1H, dd, J 5.0 and 16.5 Hz, αC$_7$H), 4.35 and 5.30 (2H, 2d, J 15.0 Hz, CH$_2$Ph), 4.65 (1H, dd, J 2.5 and 5.2 Hz, C$_6$H), 7.32 (5H, s, C$_6$H$_5$) ppm.

EXAMPLE 8

(6R) 5-Thia-1,4-diazabicyclo[4.2.0]octane-2-isopropylidene-4-benzyl-3,8-dioxo5,5-dioxide a) (2R) 1(1'-Carboxyl-2'-methyl-prop-1'-enyl)-2-benzylamino-sulfonyl-4-oxoazetidine (338 mg, 1 mmole) was dissolved in thionyl chloride (3 ml) and stirred at room temperature for 2 hours. The excess of thionyl chloride was evaporated in a water pump vacuum. The dry residue was dissolved in methylene chloride (10 ml), stirred for additional 30 minutes and washed with water, saturated sodium bicarbonate solution, dried over sodium sulfate and evaporated to a dry residue. Crystallization from 96% ethanol yielded 183 mg (57%) of the product: m.p. 160°–162° C.; $R_f$ 0.80 (C$_6$H$_6$:EtOAc=3:1);

IR (KBr): 1780vs, 1700s, 1620m, 1360s, 1340vs, 1270m, 1230s, 1215s, 1165vs cm$^{-1}$;

300 MHz $^1$H NMR (CDCl$_3$) δ:2.07 and 2.32 (6H, 2s, CMe$_2$), 3.52 (1H, dd, J 2.2 and 15.2 Hz, βC$_7$H), 3.58 (1H, dd, J 4.8 and 15.2 Hz, αC$_7$H), 4.86 (1H, 2d, J 2.2 and 4.8 Hz, C$_6$H), 4.99 (2H, s, CH$_2$Ph), 7.30–7.48 (5H, m, C$_6$H$_5$) ppm.

m/e 320 (M+).

b) The same product was formed by heating (2R) 1(1'-carboxyl-2'-methyl-prop-1'-enyl)-2-benzylaminosulfonyl-4-oxo-azetidine in acetic anhydride. After azeotropic removal of the excess of acetic anhydride with benzene, the dry residue was treated as in a).

c) The same product was formed by oxidation of (5R,6R) or (5S,6R) 5-thia-1,4-diazabicyclo[4.2.0]octane-2-isopropylidene-4-benzyl-3,8-dioxo-5-oxide or a mixture thereof with oxidants such as potassium permanganate, hydrogen peroxide or m-chloroperbenzoic acid.

EXAMPLE 9

(6R) 5-Thia-1,4-diazabicyclo[4.2.0]octane-2-isopropylidene-4(5'-methyl-isoxazole-3'-yl)-3,8-dioxo-5,5-dioxide (2R) 1(1'-carboxyl-2'-methyl-prop-1'-enyl)-2-[(5'-methyl-isoxazole-3'-yl)-aminosulfonyl]-4-oxo-azetidine (329 mg, 1 mmole) was dissolved in thionyl chloride (3 ml) and treated as disclosed in Example 8a. 112 mg (36%) of the product were obtained: m.p. 170°–175° C.; $R_f$ 0.65 (C$_6$H$_6$:EtOAc=3:1);

IR (KBr): 1800vs, 1715s, 1610m, 1360vs, 1260m, 1210m, 1180vs, 1100 cm$^{-1}$;

300 MHz $^1$H NMR (CDCl$_3$) δ:2.15 and 2.35 (6H, 2s, CMe$_2$), 2.50 (3H, s, Me-isoxazole), 3.59 (1H, dd, J 2.5 and 15.9 Hz, βC$_7$H), 3.73 (1H, dd, J 4.5 and 15.9 Hz, αC$_7$H), 5.15 (1H, 2d, J 2.5 and 4.5 Hz, C$_6$H), 6.17 (1H, s, H-isoxazole) ppm.

m/e 311 (M+).

EXAMPLE 10

(6R) 5-Thia-1,4-diazabicyclo[4.2.0]octane-2-isopropylidene-7,7-dibromo-3,8-dioxo-5,5-dioxide To a suspension of aluminum trichloride (400 mg, 3 mmole) in methylene chloride (15 ml) at 0° C. a solution of (2R) 1(1'-benzyloxycarbonyl-2'-methyl-prop-1'-enyl)-2-[(5'-methyl-isoxazole-3'-yl)-amino-sulfonyl]-3,3-dibromo-4-oxo-azetidine (577 mg, 1 mmole) in methylene chloride (15 ml) and then anisole (648 mg, 6 mmole) were added and the mixture was stirred at room temperature for half an hour. The reaction mixture was diluted with ethyl acetate, washed with diluted hydrochloric acid and extracted with a 5% aqueous sodium bicarbonate solution. The aqueous extract was acidified with hydrochloric acid and extracted with ethyl acetate. The organic extract was washed with water, dried (Na$_2$SO$_4$) and evaporated. 323 mg (83.3%) of a crystal product were obtained: m.p. 108°–110° C.; $R_f$ 0.53 (EtOAc:MeOH=3:1);

IR (film): 1805vs, 1705s, 1630m, 1380m, 1285m, 1130m, 820s, cm$^{-1}$;

300 MHz $^1$H NMR (CDCl$_3$) δ:2.05 and 2.37 (6H, 2s, CMe$_2$), 3.28 and 3.26 (1H, 2s, NH), 6.27 (1H, s, C$_6$H) ppm.

EXAMPLE 11

(6R,7R) 5-Thia-1,4-diazabicyclo[4.2.0]octane-2-isopropylidene-4(5'-methyl-isoxazole-3'-yl)-7-phenoxyacetamido-3,8-dioxo-5,5-dioxide (2R,3R) 1(1'-Carboxyl-2'-methyl-prop-1'-enyl)-2-[(5'-methyl-isoxazole-3'-yl)-aminosulfonyl]-3-phenoxyacetamido-4-oxo-azetidine (146 mg, 0.3 mmole) was dissolved in methylene chloride (5 ml) with the addition of triethylamine (34 mg, 0.34 mmole). To the solution ethyl chloroformate (37 mg, 0.34 mmole) was added at the temperature of −10° C. and the reaction mixture was treated as in Example 5.94 mg (67,3%) of the product were obtained, which crystallized with the addition of methanol; m.p. 138°–139° C.; $R_f$ 0.60 (CH$_2$Cl$_2$:EtOAc=5:3);

IR (KBr): 3450w, 1810m, 1715s, 1610m, 1535m, 1495m, 1430m, 1380m, 1370m, 1230m, 1170s cm$^{-1}$;

300 MHz $^1$H NMR (CDCl$_3$) δ:2.15 and 2.38 (6H, 2s, CMe$_2$), 2.50 (3H, s, Me-isoxazole), 4.55 and 4.59 (2H, ABq, J 15.3 Hz, OCH$_2$), 5.43 (1H, d, J 4.5 Hz, C$_6$H), 6.14 (1H, s, CH-isoxazole), 6.34 (1H, dd, J 4.5 and 10.5 Hz, C$_7$H), 6.91–7.34 (5H, m, OC$_6$H$_5$), 7.96 (1H, d, J 10.5 Hz, CONH) ppm.

EXAMPLE 12

(6R,7R) 5-Thia-1,4-diazabicyclo[4.2.0]octane-2-isopropylidene-4(5'-methyl-isoxazole-3'-yl)-7-[3'-(o-chlorophenyl)-5'-methyl-isoxazole-4'-yl]acetamido-3,8-dioxo-5,5-dioxide To a solution of cloxacillin sodium (4.76 g, 10 mmole) in dimethylformamide (300 ml), α-bromo-m-xylene (1.37 ml, 10 mmole) was added at room temperature under stirring. The reaction mixture was heated to 65° C. and stirred for 7 hours. After cooling to room temperature, the reaction solution was added drop by drop onto ice (500 ml) and stirred for 30 minutes. The aqueous solution was extracted with dichloromethane (2×500 ml). The organic extracts were collected and evaporated under reduced pressure to a bright yellow liquid (5.08 g, 94.2%). The chromatography on a silica gel column and the eluting with a benzene/ethyl acetate mixture as the eluent, of the crude product (520 mg) yielded 265 mg (51%) of pure 6-(3'-o-chlorophenyl-5'-methyl-isoxazole-4'-yl)-carboxamido-penicillinate m-methyl benzyl ester [$R_f$ 0.50 (benzene:ethyl acetate=5:1); IR (film): 3395m, 1785vs, 1740s, 1670vs, 1605s, 1500s, 1390m, 1295m, 1260m, 1205s, 1185s, 1045s, 970m, 770s, 755vw, 735w cm$^{-1}$; 90 MHz $^1$H NMR (DMSO-d$_6$) δ:1.48 and 1.62 (6H, 2s, CMe$_2$), 2.44 and 2.78 (6H, 2s, Me-Ph and Me-isoxazole), 4.53 (1H, s, C$_3$H), 5,28 (2H, s, CH$_2$-Ph), 5.58–5.80 (2H, m, C$_5$H and C$_6$H), 7.12–7.41 (8H, 2m, 2 C$_6$H$_4$), 8.39 (1H, d, J 2.9 Hz) ppm].

The obtained penicillin ester (4.055 g, 7.5 mmole) was dissolved in glacial acetic acid (12 ml) and to the solution hydrogen peroxide (1.0 ml, 8.25 mmole) was added. The reaction mixture was stirred for about 17 hours at room temperature and then added drop by drop onto ice (400 ml). The suspension was stirred for about 3 hours, filtered, washed with water and dried in air. 2.43 g (58.3%) of chromatographically pure (5R,6R) 6-(3'-o-chlorophenyl-5'-methyl-isoxazole-4'-yl)-carboxamido-penicillinate sulfoxide m-methyl benzyl ester were obtained. For analysis the product was recrystallized from ethyl acetate [m.p. 128°–9° C.; $R_f$ 0.7 (benzene:ethyl acetate=1:1); IR (CH$_2$Cl$_2$): 3360m, 1785vs, 1740–1720bs, 1655s, 1590s, 1490s, 1365m, 1200m, 1035m cm$^{-1}$; 90 MHz $^1$H NMR (CDCl$_3$) δ:1.04 and 1.56 (6H, 2s, CMe$_2$), 2.35 and 2.73 (6H, 2s, Me-Ph and Me-isoxazole), 4.53 (1H, s, C$_3$H), 4.95 (1H, d, J 4.7 Hz, C$_5$-H), 5.16 (2H, 2d, J 2.3 and 15.6 Hz, C$_2$H-Ph), 6.11 (1H, dd, J 4.7 and 10.4 Hz, C$_6$H), 6.91 (1H, d, J 10.4 Hz, NH), 7.17–7.34 (4H, m, C$_6$H$_4$) and 7.39–7.55 (4H, m, C$_6$H$_4$-Cl) ppm]. Analysis: found: C 58.64%, H 4.98%, Cl 6.55%, N 7.38%, S 5.5%; calc.: C 58.32%, H 4.71%, Cl 6.38%, N 7.56%, S 5.77%.

The obtained sulfoxide (2.0 g, 3.6 mmole) was subjected to a reaction with N-chlorosuccinimide (0.53 g, 3.9 mmole) in dry toluene (180 ml) in the presence of calcium oxide (1.22 g, 21.6 mmole). The suspension was heated at the boiling temperature in a nitrogen stream for 90 minutes, cooled to 15° C. and 3-amino-5-methyl-isoxazole (1.06 g, 10.8 mmole) was added. The reaction mixture was stirred at room temperature for 3 hours and filtered. The filtrate was extracted with water (3×50 ml); the organic part was dried (Na$_2$SO$_4$), filtered and evaporated under reduced pressure. The residue was dissolved in methylene chloride (20 ml) and stirred with triethylamine (0.48 ml) for 2 hours at room temperature. It was extracted with 0.1N hydrochloric acid (5 ml), then with water (10 ml) and the organic extract was dried (Na$_2$SO$_4$), filtered and evaporated in vacuo. The chromatography on a silica gel column and eluting with methylene chloride/ethyl acetate solvent mixture yielded 1.24 g (55.6%) of (2R,3R) 1(1'-m-methylbenzyl oxycarbonyl-2'-methyl-prop-1'-enyl)-2-[(5'-methyl-isoxazole-3'-yl)aminosulfinyl]-3-[(3'-o-chlorophenyl-5'-methyl-isoxazole-4-yl)carboxamido]-4-oxo-azetidine [$R_f$ 0.21 (CH$_2$Cl$_2$:EtOAc=4:1); m.p. 94°–96° C.; 90 MHz $^1$H NMR (CDCl$_3$) δ:1.95 and 2.22 (6H, 2s, CMe$_2$), 2.33 and 2.35 (6H, 2s, 2 Me-isoxazole), 2.77 (3H, s, Me-Ph), 4.96 (1H, d, J 4.5 Hz, C$_2$H), 5.13 (2H, bs, OCH$_2$), 5.61 (1H, dd, J 4.5 and 8.5 Hz, C$_3$H), 5.72 (1H, s, CH-isoxazole), 6.69 (1H, d, J 8.5 Hz, CONH), 7.04–7.55 (8H, m, 2 C$_6$H$_4$) ppm].

Oxidation with hydrogen peroxide in methylene chloride yielded (2R,3R) 1-(1'-m-methylbenzyl oxycarbonyl-2'-methyl-prop-1'-enyl)-2-[(5'-methyl-isoxazole-3'-yl)aminosulfonyl]-3-[(3'-o-chlorophenyl-5'-methyl-isoxazole-4-yl)carboxamido]-4-oxo-azetidine in a 85.8% yield [$R_f$ 0.55 (CH$_2$Cl$_2$:Me-OH=10:1); IR (film): 3410w, 3160vw, 3070wv, 1795vs, 1735w, 1685bs, 1620s, 1640m, 1580bs, 1420w, 1300m, 1270m, 1220m, 1170m, 1120m, 1060m, 770m, 740m cm$^{-1}$; 300 MHz $^1$H NMR (CDCl$_3$) δ:1.84 and 2.11 (6H, 2s, CMe$_2$), 2.26 and 2.33 (6H, 2s, 2Me-isoxazole), 2.72 (3H, s, CH$_3$-Ph), 5.01 (2H, bs, OCH$_2$), 5.36 (1H, d, J 5.0 Hz, C$_2$H), 5.71–5.92 (2H, m, C$_3$H and CH-isoxazole), 6.41 (1H, d, J 10 Hz, CONH), 7.01–7.62 (8H, m, 2C$_6$H$_4$) ppm]. The obtained sulfonamide (0.549 g, 0.82 mmole) was then dissolved in methanol (55 ml) and hydrogenated for 5 hours at the pressure of 4.5 bar using 10% Pd on carbon (250 mg). The reaction mixture was filtered and the mother liquor was evaporated in vacuo. The residue was dissolved in methylene chloride (20 ml) and water (20 ml) and the pH was adjusted to 8.5 by adding sodium bicarbonate. The aqueous extract was separated, shaken with fresh methylene chloride, a new amount of methylene chloride (15 ml) was added and the pH was adjusted to 2.2 by adding hydrochlorid acid. The organic extract was separated, dried (Na$_2$SO$_4$), filtered and evaporated in vacuo. 0.121 g (26.1%) of (2R,3R) 1-(1'-carboxyl-2'-methyl-prop-1'-enyl)-2-[(5'-methyl-isoxazole-3'-yl)aminosulfonyl]-3-[(3'-o-chlorophenyl-5'-methyl-isoxazole-4'-yl)-acetamido]-4-oxo-azetidine [R$_f$ 0.79 (EtoAc:HOAc:H$_2$O=6:1:1); IR (KBr): 3460–3380bm, 1785vs, 1725m, 1610vs, 1560m, 1505vs, 1460vs, 1390m, 1200m, 1160s, 1050vw, 980w, 705m cm$^{-1}$]. To a solution (330 mg, 0.58 mmole) of the obtained acid in methylene chloride (6 ml) and triethylamine (65 mg, 0.64 mmole), cooled to −10° C., ethyl chloroformate (69 mg, 0.64 mmole) was added under stirring. The obtained reaction mixture was stirred for 1 hour at −10° C. and for 2 hours at room temperature and then it was shaken with water (1×6 ml). The organic layer was dried (MgSO$_4$), filtered and evaporated under reduced pressure to a dry residue. The product was chromatographed on a silica gel column with a methylene chloride/ethyl acetate solvent mixture. 74 mg (23%) of a powdery product were obtained; R$_f$ 0.64 (CH$_2$Cl$_2$:EtOAc=4:1);

IR(film)ν: 3410w, 1795vs, 1720s, 1690s, 1590s, 1520s, 1435m, 1370vs, 1300w, 1275m, 1225s, 1165s, cm$^{-1}$;

300 MHz $^1$H NMR (CDCl$_3$) δ: 2.10 and 2.33 (6H, 2s, CMe$_2$), 2.49 (3H, s, Me-isoxazole), 2.74 (3H, s, Me-isoxazole), 5.28 (1H, d, J 4.2 Hz, C$_6$H), 6.07 (1H, s, CH-isoxazole), 6.35 (1H, dd, J 4.2 and 9.6 Hz, C$_7$H), 6.65 (1H, d, J 9.6 Hz, CONH), 7.5–7.6 (4H, m, C$_6$H$_4$) ppm.

I claim:

1. 5-Thia-1,4-diazabicyclo[4.2.0]octane-3,8-dioxo β-lactam analogs of the formula I

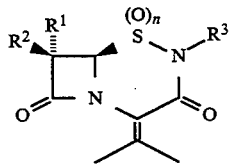

wherein
R$^1$ is hydrogen or halo;
R$^2$ is hydrogen, halo, amino, PhCH$_2$CONH, PhOCH$_2$CONH, phthalimido, o-MeNHCO-C$_6$H$_4$-CONH, isoxazolylcarboxamido;
R$^3$ is hydrogen, alkyl, benzyl, or 5-methyl-isoxazole-3-yl, and
n may be 1 or 2.

2. The compound according to claim 1 wherein R$^1$ is hydrogen, R$^2$ PhCH$_2$CONH, R$^3$PhCH$_2$ and n is 2.

3. The compound according to claim 1, wherein R$^1$ is hydrogen, R$^2$ is PhCH$_2$CONH, R$^3$ is 5-methyl-isoxazole-3-yl and n is 2.

4. The compound according to claim 1, wherein R$^1$ is hydrogen, R$^2$ is PhCH$_2$CONH, R$^3$ is methyl and n is 2.

5. The compound according to claim 1, wherein R$^1$ is hydrogen, R$^2$ is phthalimido, R$^3$ is 5-methyl-isoxazole-3-yl and n is 2.

6. The compound according to claim 1, wherein R$^1$ is hydrogen, R$^2$ is o-MeNHCO-C$_6$H$_4$-CONH, R$^3$ is methyl and n is 2.

7. The compound according to claim 1, wherein R$^1$ is hydrogen, R$^2$ is hydrogen, R$^3$ is PhCH$_2$ and n is 2.

8. The compound according to claim 1, wherein R$^1$ is hydrogen, R$^2$ is hydrogen, R$^3$ is 5-methyl-isoxazole-3-yl and n is 2.

9. The compound according to claim 1, wherein R$^1$ is bromo, R$^2$ is bromo, R$^3$ is hydrogen and n is 2.

10. The compound according to claim 1, wherein R$^1$ is hydrogen, R$^2$ is PhOCH$_2$CONH, R$^3$ is 5-methyl-isoxazole-3-yl and n is 2.

11. The compound according to claim 1, wherein R$^1$ is hydrogen, R$^2$ is 3-(o-chlorophenyl)-5-methyl-isoxazole-4-yl, R$^3$ is 5-methyl-isoxazole-3-yl and n is 2.

12. The compound according to claim 1, wherein R$^1$ is hydrogen, R$^2$ is hydrogen, R$^3$ is PhCH$_2$ and n is 1.

13. A process for preparing 5-thia-1,4-diazabicyclo[4.2.0]octane-3,8-dioxo analogs of β-lactam of the formula I, wherein the radicals have the meanings as given in claim 1, characterized in that amides of 4-oxoazetidine-2-sulfonic acids or -sulfinic acids of the formula II

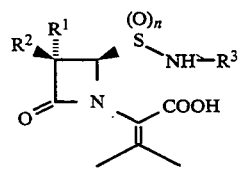

wherein
R$^1$ is hydrogen or halo;
R$^2$ is hydrogen, halo, PhCH$_2$CONH, PhOCH$_2$CONH, phthalimido, o-MeNHCO-C$_6$H$_4$CONH, isoxazolylcarboxamido;
R$^3$ is alkyl, benzyl, or 5-methyl-isoxazole-3-yl, and
n may be 1 or 2,
are subjected to the reaction with dicyclohexylcarbodiimide or thionyl chloride or ethyl chloroformate or acetic anhydride or aluminum trichloride, whereat the carboxyl group of the compound II is converted into an active ester or acid chloride or mixed anhydride, which in situ in a dry organic aprotic solvent are intramolecularly cyclized or are isolated and then cyclized under conventional reaction conditions, followed by the treatment of the reaction mixture and isolation of the products by means of well-known methods.

14. A pharmaceutical composition comprising an antimicrobially effective amount of a compound of claim 1 together with a pharmaceutically acceptable carrier.

* * * * *